United States Patent [19]

Girard et al.

[11] Patent Number: 4,968,627

[45] Date of Patent: Nov. 6, 1990

[54] DNA FRAGMENTS CODING AN IMMUNOGEN PEPTIDE LIABLE OF INDUCING IN VIVO SYNTHESIS OF ANTI-POLIOVIRUS ANTIBODIES

[75] Inventors: Marc Girard; Sylvie van der Werf, both of Paris, France

[73] Assignee: Institut Pasteur, Paris, France

[21] Appl. No.: 886,754

[22] Filed: Jul. 15, 1986

Related U.S. Application Data

[63] Continuation of Ser. No. 464,175, Feb. 7, 1983, abandoned.

[30] Foreign Application Priority Data

Feb. 8, 1982 [FR] France ................................ 82 02013

[51] Int. Cl.[5] ....................... C12P 19/34; C12N 15/00; C07H 15/12

[52] U.S. Cl. .................................. 435/320; 435/172.3; 435/91; 536/27; 935/11; 935/12; 935/27; 935/29; 935/32; 935/41; 935/65; 424/86; 424/89

[58] Field of Search ....................... 435/172.3, 320, 91, 435/235; 536/27; 935/11, 12, 27, 29, 32, 41, 65; 424/86, 89

[56] References Cited

U.S. PATENT DOCUMENTS 4,442,205 4/1984 Hamer et al. ..................... 935/32 X 4,694,072 9/1987 Girard et al. ................... 530/327 X 4,719,177 1/1988 Baltimore et al. ................ 935/12 X 4,751,083 6/1988 Baltimore et al. ................ 435/68 X

OTHER PUBLICATIONS van der Werf, S. et al., *Proc. Natl. Acad. Sci.,* vol. 78, pp. 5983–5987, 1981.

Racaniello, V. et al., *Proc. Natl. Acad. Sci.,* vol. 78, pp. 4887–4891, 1981.

Kitamura, N. et al., *Nature,* vol. 291, pp. 547–553, 1981.

Pavlakis, G. et al., *Proc. Natl. Acad. Sci.* vol. 78, pp. 7398–7402, 1981.

Chow, M. et al., *Proc. Natl. Acad. Sci.,* vol. 79, pp. 7518–7521, Dec. 1982.

Meloen et al., *J. Gen. Virol.,* vol. 45, pp. 761–763 (1979).

Blondel et al., *C. R. Acad. Sc. Paris,* vol. 294, pp. 91–94 (1982).

Mandel et al., *Advances in Virus Research,* vol. 23, pp. 205–269 (1978).

*Primary Examiner*—Robin L. Teskin

*Attorney, Agent, or Firm*—Oblon, Spivak, McClelland, Maier & Neustadt

[57] ABSTRACT

DNA fragment capable of coding for an immunogenic peptide capable of inducing in vivo antibody reacting with anti-poliovirus. It possesses up to the order of 1.2 kilobase pairs and contains a nucleotide sequence coding for the poliovirus VP1 protein.

9 Claims, 6 Drawing Sheets

FIG. 1

```
      3210      3220      3230      3240      3250      3260      3270      3280      3290      3300
CTGTTAGAGTAGTCAATGATCAAACCCGACCAAGGTCACCTCCAAAATCAGAGTGTATCTAAAACCAAACACATCAGAGTCTGGTGCCGCCGTCCACC
                   ^^    ^
                   BCL1  SAU3A                                                              BCER
                   SAU3A 3310      3320      3330      3340      3350      3360      3370      3380
GAGGGCAGTGGGCGTACTACGGCCCTGGAGTGGATTACAAGGATGGTACGCTTACACCCCTCTCCACCAAGGATCTGACCACATAT
     ^       ^                                  ^                        ^           →
     RSA1    HAE111                             RSA1                     SAU3A       VP1
```

```
          2310      2320      2330      2340      2350      2360      2370      2380      2390      2400
CCATAGATGATAGTTTCACCGAAGGCGGATACATCAGGTCTTCTACCAAACTAGAGAATAGTCGTCCCTCTTTCGACACCCAGAGAGATGGACATCCTTGG
                                                                                       ^
                                                                                       TAQ1

2410      2420      2430      2440      2450      2460      2470      2480      2490      2500
TTTTGTGTCAGGCGTGTAATGACTTCAGGTGCGCTTGTTGCGAGATACCACACACATATAGAGCAAAAA AGCGCT AGCACA GGTTAGGTCAGATGCTTGAA
                     ^                                                ^^          VP3 ──→ VP1
                     HHA1                                             HAE11
                                                                      HHA1

2510      2520      2530      2540      2550      2560      2570      2580      2590      2600
AGCATGATTGACAACACAGTCCGTGAAACGGTGGGGGCGGCAACA TCTAGA GACGCTCTCCCAAACACTGAAGCCAGTGGACCAACACACTCCAAGGAAA
                                              ^
                                              XBA1

2610      2620      2630      2640      2650      2660      2670      2680      2690      2700
TTCCGGCACTCACCGGCAGTGGAAACTGGGGCCACAAATCCACTAGTCCCTTCTGATACAGTGCAAACCAGACATGTTGTACAAGATAGGTCAAGGTCAGA
 ^                                           ^^^                                              ^
 HPA11                                       HAE111                                           RSA1

2710      2720      2730      2740      2750      2760      2770      2780      2790      2800
GTCTAGCATAGAGTCTTTCTTCGGCGGGGTGCATGCGTGACCATTATGACCGTGGATAACCCAGCTTCCACCACGAATAAGGATAAGCTATTGCAGTG
       ^^^                                                                                    ^
       BCER                                                                                   ALU1
       HHA1
       BCER 2810      2820      2830      2840      2850      2860      2870      2880      2890      2900
TGGAAGATCACTTATAAAGATACTGTCCAGTTACGGAGGAAATTGGAGTTCTTCACCTAT TCTAGA TTTGATATGGAACTTACCTTTGTGGTTACTGCAA
 ^                                                           ^
 SAU3A                                                       XBA1
```

```
       2910      2920      2930      2940      2950      2960      2970      2980      2990      3000
ATTTCACTGAGAGACTAACAATGGGCATGCCTTAAATCAAGTGTACCAAATTATGTACGTACCACCAGGCCTCAGTGCCCGAGAAATGGGACGACTACAC
                                              ^              ^           ^          ^
                                              RSA1           RSA1        HAE11       AVA1
                                                                         HHA1

3010      3020      3030      3040      3050      3060      3070      3080      3090      3100
ATGGCAAACCTCATCAAATCCATCAATCTTTTACACCTACGAACAGCTCCAGCCCGGATCTCGTATGTTGGTATTTCGAACGCCTATTCACAC
                                          ^                ^        ^                    ^
                                          ALU1             HPA11    KPN1                 ASU11
                                                           SAU3A    RSA1                 TAQ1

3110      3120      3130      3140      3150      3160      3170      3180      3190      3200
TTTTACGACGGTTTTTCCAAAGTACCACTGAAGGACCAGTCGGCAGACTAGGTGACTCCCTTTATGGTGCAGCATCTCTAAATGACTTCGGTATTTTGG
        ^
        RSA1

3210      3220      3230      3240      3250      3260      3270      3280      3290      3300
CTGTTAGAGTAGTCAATGATCAACAACCCGACCAAGGTCACCTCCAAAATCAGAGTGTATCTAAAACACATCCAAACCAAACATCAGAGTCTGGTGCCGGTCCACC
              ^                                                                                        ^
              BCL1                                                                                     BCER
              SAU3A 3310      3320      3330      3340      3350      3360      3370      3380      3390      3400
GAGGCAGTGGCGTACTACGGCCCTGGAGTGGATTACAAGGATGTAAGGCTTACACCCCTCTCCACCAAGGATCTGACCACATAGGATTCGGACACCAA
    ^       ^                                                    ^                     |->
    RSA1    HAE111                                               SAU3A                  VP1

3410      3420
AACAAAGCGGTGTACACTGCAGG
        ^          ^
        RSA1       PST1
```

FIG. 4

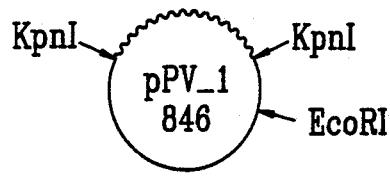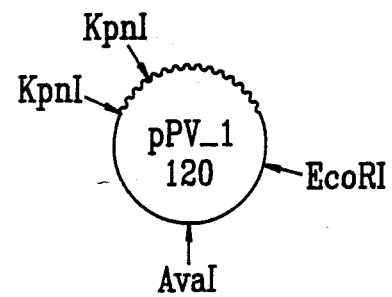
FIG.5a  FIG.5b
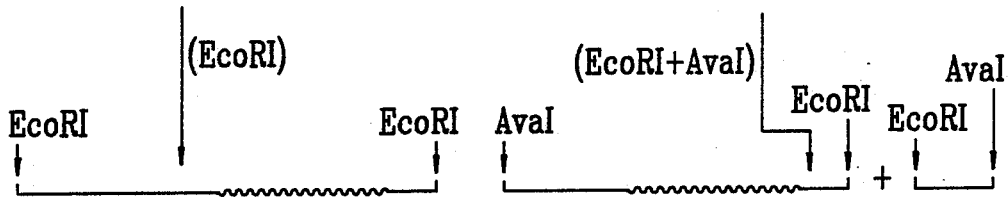
FIG.5c  FIG.5e
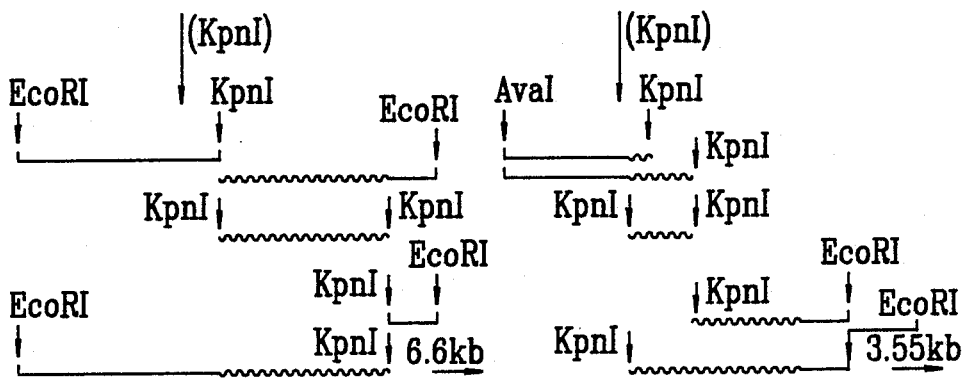
FIG.5d  FIG.5f
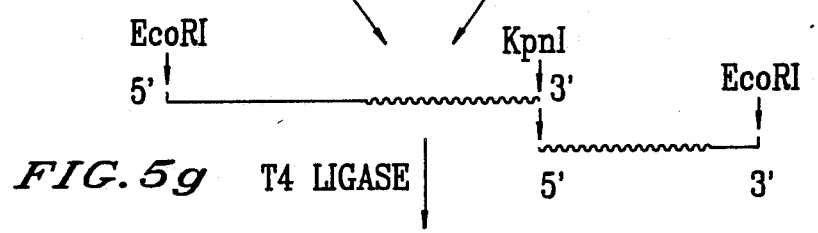
FIG.5g  T4 LIGASE
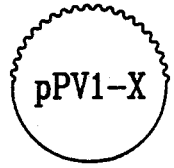
FIG.5h HaeII
PstI

DNA FRAGMENTS CODING AN IMMUNOGEN PEPTIDE LIABLE OF INDUCING IN VIVO SYNTHESIS OF ANTI-POLIOVIRUS ANTIBODIES

This application is a continuation of application Ser. No. 464,175, filed Feb. 7, 1983, now abandoned.

FIELD OF THE INVENTION

The invention relates to a DNA fragment coding for an immunogen peptide "liable of" inducing in vivo the formation of antipoliovirus antibodies. It relates more particularly to DNA fragments of this type having, at the level of the genetic information that they contain, parts in common with the polioviruses, preferably, but not exclusively of the PV-1 type, whilst being however of small size. In other words, the invention relates to a DNA fragment coding for an antigenic determinant belonging normally to peptides coded by the RNA of the poliovirus or by corresponding cDNAs, this antigenic determinant playing an essential role at the level of the antigenic properties of the expression products of natural viral RNA.

GENERAL DESCRIPTION OF THE INVENTION

The DNA fragments according to the invention have a length not exceeding that of a DNA fragment comprising of the order of 1.2 kb or kbp (kilobase pairs), these fragments being more particularly characterized in that they contain a nucleotide sequence coding for the VP1 protein or for the part of the latter which codes for that or those of the antigenic determinants which can be considered as essentially responsible for the immunogenicity and the immunological specifity of the VP-1 protein of the poliovirus.

The invention relates also to the vectors, particularly plasmids or phages, which contain at one of their specific restriction sites, one of the fragments such as described above, these fragments being thus heterological with respect to what can then be termed as the "body" of the vector (DNA sequence(s) peculiar to the vector itself).

The invention arises from the discovery that the peptide or protein fragment coded by the DNA fragment represented in the succession of the accompanying figures 1 and 2, is capable of forming antigen - antibody complexes with monoclonal antibodies or polyclonal neutralizing serums, prepared by injection into the animal of whole poliovirus fixed with formol (serum of D specificity).

The invention, of course, also relates to DNA fragments which may be somewhat larger, for example that which is normally bounded by PstI sites at the 2243 and 3417 positions (with respect to the 5' end), in the clonable DNA fragment of the poliovirus described in the article of Sylvie Van Der WERF and other authors entitled "Molecular cloning of the genome of poliovirus" in Proc. Nat. Acad. Sci. U.S.A. volume 78, N° 10, pp.5983–5987 October 1981. The sequence of nucleotides of this DNA fragment is indicated in the succession of FIGS. 3 and 4.

The sequence of nucleotides according to the invention coding VP1 protein may be obtained from a precursor containing it. FIGS. 5a to 5h show diagrammatically a method of production of such a precursor obtained from the clones pPVI-846 and pPVI-120 described in the above-indicated article. The procedure of recombination of the two above-indicated clones to obtain the clone pPVl-X is described below.

FIGS. 6a to 6f show diagrammatically the steps of a method of producing a plasmid containing the essential of the genetic information of the DNA sequence, such as results from FIGS. 1 and 2.

BRIEF DESCRIPTION OF THE FIGURES:

FIGS. 1 and 2 depict DNA fragments corresponding to the PV-1 genome which code for a protein or peptide which is capable of complexing with poliovirus neutralizing antibodies.

FIGS. 3 and 4 depict the nucleotide sequence corresponding to from position 2243 to position 3417 of the PV-1 genome.

FIGS. 5a to 5h depict diagrammatically the steps required to obtain clone p PV1-X.

Figure 6A:
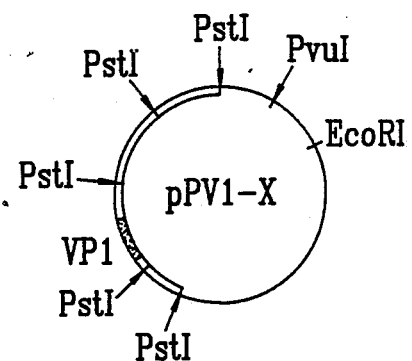
FIGS. 6a to 6f depict diagrammatically a method for producing a plasmid containing PV-1 DNA sequences, such as the sequences of FIGS. 1 and 2.
Figure 6B:
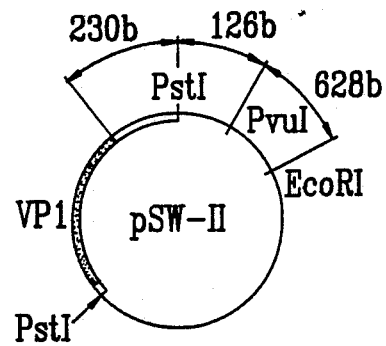
Figure 6C:
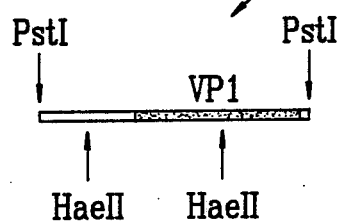

1. Hydrolysis of DNAs Cloned by Restriction Enzymes 1.1 The DNA of the pPVI-846 plasmid is hydrolysed completely by EcoRT. The linear form of the plasmid DNA so obtained (FIG. 5c) is hydrolysed by partial digestion with Kpn I; the fragments obtained (FIG. 5d) are separated by electrophoresis on 0.7% agarose gel.

The fragment of size 6.6 kbp is selected. It represents in fact the sequence of the plasmid pBR322 of the EcoRI site at the Pst I site, extended by that of the DNA corresponding to the sequence of the poliovirus which extends from the nucleotide ($1^{35}$) to the nucleotide 3050 (2nd Kpn I site).

1.2 The DNA of the clone pPVI-120 is hydrolysed in a complete digestion by AvaI and EcoRI, thus forming 2 fragments of different sizes (FIG. 5e). The DNA is then hydrolysed partially by Kpn I . The fragments so obtained (FIG. 5f) are separated by electrophoresis on 0.7% agarose gel.

The fragment of size 3.55 kbp is selected. It represents in fact the sequence of the cDNA of the polyovirus extending from the; nucleotide 3050 (2nd Kpn I site) to the nucleotide 5650 approximately, extended by that of the 752 base pairs of the Pst I-EcoRI segment of the plasmid pBR322.

2. Extraction of the DNA Fragments from the Gels 2.1 The fragments are made visible in the gels by dyeing with ethidium bromide; those of the desired size are extracted from the gels by electroelution in a dialysis bag.

2.2 The material so obtained is purified and concentrated.

3. Linking to Each Other of the Fragments through their Sticky Ends (Recombination)

The two fragments selected, derived from the clones pPVI-846 and pPVI-120 as described above, are mixed and linked by means of the DNA ligase of phage T4. The sticky ends formed at the cleavage points by EcoRI and KpnI and borne at each extremity of the two fragments facilitate their linking to each other and ensure that the latter linking takes place in the desired direction only (FIGS. 5g and 5h).

The genome of the plasmid pBR322 is thus constituted with neither modification nor delection in the recombinant plasmid. In particular, the regions necessary for its replication and for the expression of resistance to tetracycline are not affected.

4. Transformation of the Strain *E. Coli* 1106

The fragments of the plasmids pPVI-846 and pPVI-120 relinked through their Kpn I and EcoRI sites are contacted with competent bacteria of the E.coli 1106 strain under conditions suitable for their transformation. The bacterial colonies resistant to tetracycline and sensitive to ampicillin are selected.

5. Analysis of the New Clones 5.1 The plasmidic DNA of the tetracycline resistant bacteria is purified. Its mass is determined by electrophoresis on agarose gel. It is equal to that of the pBR322 plasmid increased by 5650 base pairs of the viral cDNA formed by recombination.

5.2 Hybridation in vitro of the cDNA so obtained with specific probes derived from the pPVI-846 and pPVI-120 clones enable verification of the presence in a single recombinant clone of the genetic material of the poliovirus originally inserted into the two parent clones.

5.3 Detailed analysis of the new clones is effected by the methods previously used for the study of the clones already characterized (physical mapping by restriction enzymes, electron microscopy, nucleotidic sequence, etc).

5.4 The cDNA borne by the recombinant plasmid (pPVl-X) bears the genetic information necessary for the synthesis of the p 1 protein, precursor of the capsid VP4 (nucleotides 741 to 975), VP2 (nucleotides 976 to 1818), VP3 (1819 to 2562) and VP1 (2563 to 3501) proteins, of the p2 protein (precursor particularly of the NCVPX protein)and of the beginning of the p3 protein. The whole includes about 5650 from among the 7432 bases of the viral genome.

The plasmid pPVI-846 has been deposited at the C.N.C.M.(i.e. the depositary of microorganisms known as the "Collection Nationale des Cultures de Microorganismes" of the Pasteur Institute of Paris, France) under N° I-155 and the plasmid 120 under n° I-156,on 19 May 1981.

The pPVI-X plasmid obtained comprises an insert containing the nucleotide sequence which codes for the VPO (nucleotides 743 to 1765), VP3 (nucleotides 1766 to 2479) and VPI (nucleotides 2480 to 3385) proteins, the sequence coding for the P2 protein (nucleotides 3386 to about 5100) and for the beginning of the P3 protein.

Starting from the pPVl-X plasmid, it is then possible to obtain a cDNA fragment coding for VP1 upon proceeding as follows:

I—ISOLATION AND RECLONING OF A cDNA FRAGMENT CONTAINING THE VP1 SEQUENCE

Figure 1:
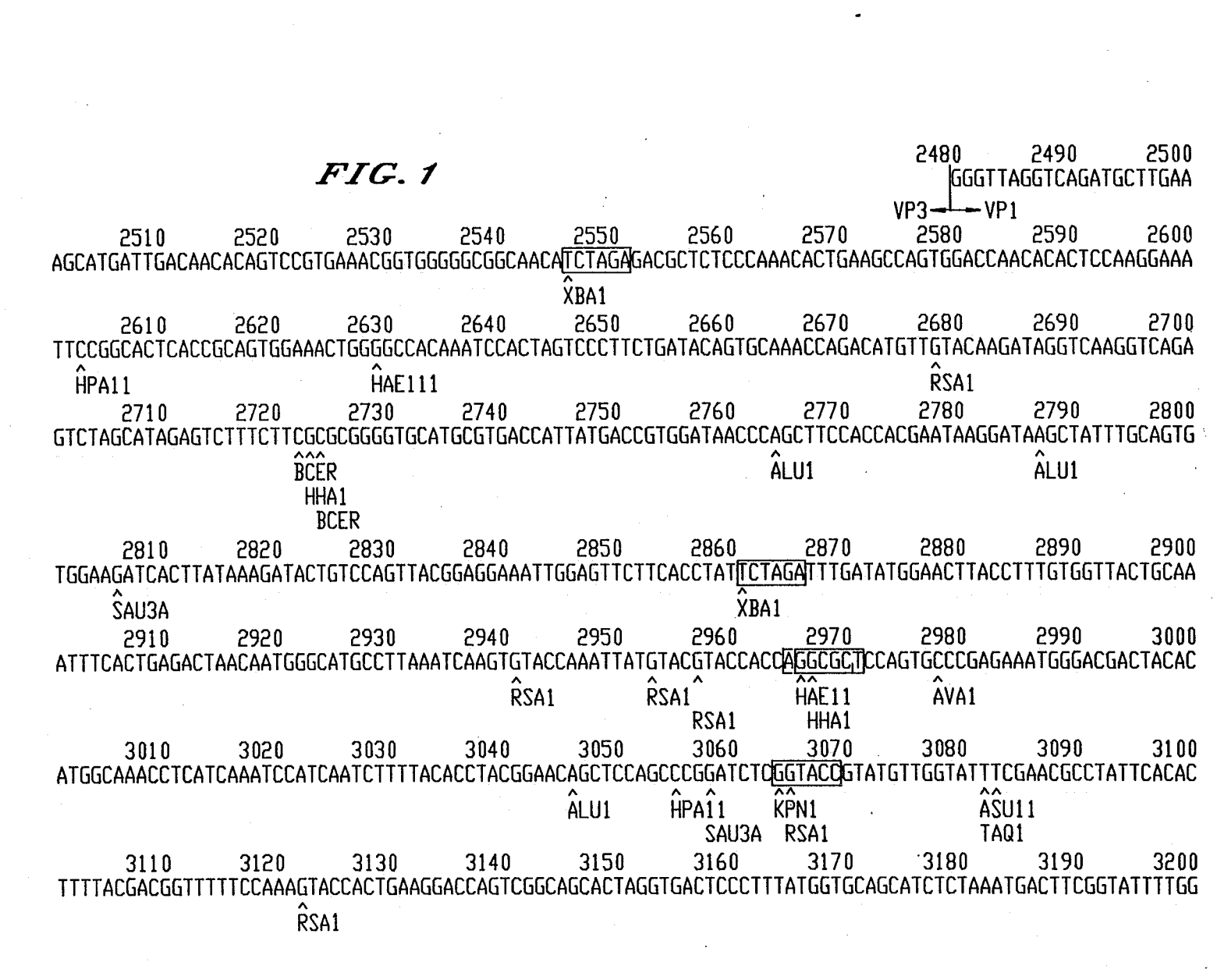

The sequence of nucleotides which codes for the VP1 protein is bounded in the viral genome, and consequently also in the insert borne by pPVl-X by two Pstl sites, located respectively 237 nucleotides upstream (position 2243) and 32 nucleotides downstream (position 3417) from the first and last nucleotides respectively of this sequence (see restriction map in the abovesaid publication and FIGS. 1 and 2).

Hence the cleavage of pPVl-X (FIG. 6*a*) by the restriction enzyme PstI generates a family of fragments having lengths corresponding respectively to 4.36 kb (body of the plasmid) and to 1.8 kb; 0.43 kb; 1.17 kb and about 2.23 kb. The fragment of 1.17 kb carries the nucleotide sequence coding for the end of VP3 and the whole of VP1. The starting nucleotide sequence of the latter fragment is $_{5'}$G T C C T C A T G T A and the end sequence thereof is G T A C A C T G C A$_{3'}$. The other PstI fragments are separated by electrophoresis on agarose gel. The strip of the gel which contains it is taken up and it is subjected to electroelution to extract the DNA therefrom. The electroelution is followed by exposure to ultraviolet light after dyeing of the gel with ethidium bromide. The fragment so prepared corresponds to the nucleotide 2248–3421 sequence of the poliovirus. It is inserted by ligation with DNA ligase at the PstI site of the pBR-322 vector plasmid previously linearized by the same enzyme. The recombinant plasmids thus formed are cloned in the 1106 strain of Escherichia coli (selection of the colonies which have become resistant to tetracycline but remain sensitive to ampicillin after transformation by the plasmid).

Analysis of their DNA by mapping with restriction enzyme enables the identification and selection of the recombinant plasmids which bear the polioviral cDNA fragment inserted in anti-clockwise direction with respect to the map of pBR-322, that is to say in the same transcriptional direction as the gene of β-lactamase (gene of resistance to ampicillin) . It should be noted that the insertion of the 2248–3421 fragment at the PstI site of pBR-322 interrupts the continuity of the nucleotide sequence, and hence inactivates the gene of the β-lactamase of the vector, yet does not enable the expression of the polioviral proteins to be ensured, owing to phase shift of the reading frame of the insert.

The plasmid having these properties is named pSW-11 (FIG. 6*b*).

II—ELIMINATION OF THE SEQUENCES CODING FOR THE TERMINAL PORTION C OF VP 3: TRIMMING OF VP 1

The pSW-11 plasmid contains 232 nucleotides of the VP3 sequence in the poliovirus cDNA, upstream of the VP1 sequence in the transcriptional direction 5→3′ sequence. This excess nucleotides can be removed according to at least two techniques:

(a) a first technique comprises controlled treatment of the 1.17 kb PstI fragment (previously extracted from pSW-11; FIG. 6*c*) by the Hae II restriction enzyme (partial digestion at the level of nucleotide 2472), then the selection by electrophoresis of the 0.945 kb HaeII-PstI fragment (FIG. 6*d*) (polioviral nucleotide 2472–3421 sequence)and recloning of this fragment in suitable plasmids. It is possible to facilitate recloning by attaching in a manner known per se, to the ends of the endtrimmed fragment, synthetic linkers consisting of short sequences of nucleotides containing a determined restriction site synthetized for example according to the technique described by R.H. SCHELLER et al, Science, Volume 196 (1977), pp 177–180. The linker selected is essentially dependant on the restriction enzyme of the expression vector.

(b) A second technique comprises linearization of the plasmid pSW-11 by complete digestion with the PvuI enzyme, exonucleolytic treatment with the Bal 31 enzyme, addition of synthetic linkers (Biolabs, Collaborative Research) and recircularization of the plasmid by DNA ligase.

The plasmids so formed are treated with the restriction enzyme corresponding to the restriction site of the linker.

Figure 6E:
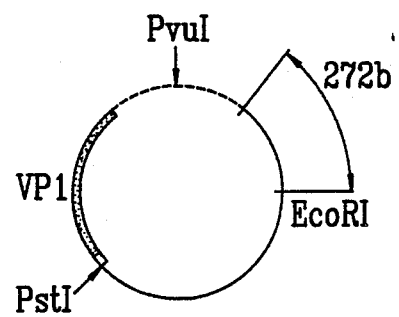
Figure 6D:
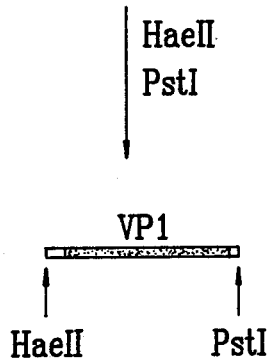

The molecules are thus opened. Their sizes are analyzed by migration on electrophoresis in agarose gel to identify those which have lost about 700 base pairs (which loss is symbolized in FIG. 6e by an arc in dotted line) that is to say a sequence which comprised about 350 base pairs on each side of the PvuI site, namely the PvuI-PstI fragment of pBR-322 and the sequence of VP3 up to VP1, on one side, and a sequence of similar length of pBR-322 from the PvuI side towards the EcoRI,site,on the other side of said PvuI site.

In this manner, it is possible to isolate a fragment one end of which coincides substantially with the end of the DNA sequence coding for VP3 or is very close thereto.

In fact, the PvuI site occured at 126 base pairs (b) from the proximal site PstI of the sequence of the 1.17kb PstI fragment and at 356base pairs from the proximal end of the cDNA fragment coding for VP1, in the plasmid pSW-11.

Figure 6F:
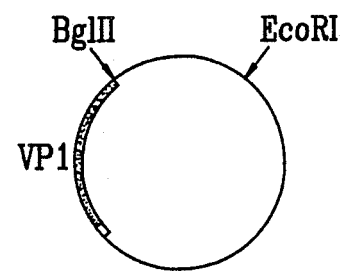

After the ligation of linkers containing for example a BglII site to the ends of the selected fragment by means of a ligase, plasmids having sizes of from 4.8 to 5 kb are selected (FIG. 6f). Those of the plasmids which contain the whole VP1 sequence, whilst having lost all or almost all of VP3 sequence are then selected, such as by determination of the nucleotide sequence of the BglII-PstI fragment of the selected plasmids. If the SANGER method is used, the fragments to be sequenced are inserted in the replicative form of the M13 phage ,the recombinant phages so constituted then being cloned, their DNA being then used to sequence the inserted fragment according to the SANGER technique. It is also possible to proceed with the determination of the nucleotide sequence as preserved according to the method of MAXAM and GILBERT.

III—INSERTION OF THE END TRIMMED FRAGMENT INTO AN EXPRESSION VECTOR

The sequence coding for VP1 includes neither initiating codon, nor terminating codon. It includes neither a promoter for its transcription, nor a signal of recognition by the ribosomes (sequence of SHINE and DALGARNO, described in GIRARD and HIRTH, Virologie Moléculaire, Edition Doin 1980, pp. 15–46 and 263–264). Its expression is hence subject to the insertion thereof in phase at the middle of the nucleotide sequence (and in any case behind the initiation AUG) of a cloned gene with its promoter (or to which there will be joined upstream, a foreign promoter). The use of linkers, as described above, enables the use of several types of different expression vectors to be envisaged according to the promoter concerned; for example of the type indicated below by way of example.

(a) Bacterial Promoters

It is particularly the case of plasmids containing the promoter-operator region of the lactose operon of *E. coli* (lac operon), followed by the portion 5' of the gene of β-galactosidase. These vectors, of the pPC type (CHARNAY et al), Nucleic Acid Research 1978, volume V,pp. 4479–4494) enable the insertion of the VP1 fragment at the EcoRI site situated at 21 nucleotides behind the initiating AUG of, the β-galactosidase. The protein to which they give rise hence includes at the N terminal end thereof the seven (or eight) first amino acids of the bacterial β-galactosidase, followed by the amino acids of VP1.

(b) Phage Promoters

This is particularly the case of the plasmids containing the promoter-operator region of the left operon ($P_L$) or of the right operon ($P_R$) of the λ phage. These vectors, respectively of the type pKC30 (ROSENBERG, Nature 1981, Volume 292, p. 128) or pRL447 (ZABEAU; derivative of pRC5 and of pLG400, the latter being described in Cell, 1980, Volume 20, pp. 543–553) enable the insertion of the fragment VP1 to be effected within the nucleotide sequence coding either for the N terminal end of the product of the gene N or for that of the product of the gene cro deposited on Feb. 8, 1982 at the C.N.C.M. under N° I-184. These vector systems are propagated at 30° C. in lysogenised bacteria by a λ phage with a thermosensitive repressor (cI 857) or in the presence of plasmids bearing the same gene (cI 857) coding for a thermosensitive repressor. They remain inactive, owing to the repressor, whilst the culture is kept at 30° C. The transfer of the culture at 42° C. is followed by the inactivation of the λ promoters ($P_L$ or $P_R$) borne by the recombinant plasmid, as a result of the inactivation of the repressor of the cl 857 gene.

(c) Viral Promoters

It is particularly the case of the use of the virus SV40 as vector. In this case, the late viral promoter is used and the VP1 fragment of the poliovirus is inserted in the place of all or part of the region coding for the tardive proteins of SV40 (VP1 or VP2). In this way substituted SV40 DNas are constructed in which the sequences coding for the capsid proteins of this virus are replaced by the sequence coding for the VP1 protein of the poliovirus. Thus, the insertion of the fragment HaeII-PstI of poliovirus described in paragraph 3 above, in place of the tardive fragment Hae II-PstI of SV40 (nucleotides from 767 to 1923) results, after phase restoration of the two sequences at the level of the HaeII site, in creating a chimerical gene possessing the VP1 sequence of the poliovirus directly linked behind and to the N terminal portion of the sequence coding for the VP2 protein of SV40.

Numerous other constructions are possible, for example by insertion of the PstI fragment of the poliovirus (1.17 kb fragment) at the PstI site (nucleotide 1923) of SV40 or by insertion of the fragment HaeII-PstI in place of the sequences AccI-BamHI(1563 to 2468) of the SV40. All the chimerical SV40's so constituted are defective. They can only grow in the presence of an assistant virus (for example a ts A30 or ts A58 type early mutant) which contributes to the production of the capsid proteins of SV40.

It is possible to contemplate partial deletions of the SV40 virus used as a vector, as described in the article of PAVLAKIS, HIZUKA, GORDEN, SEEBURG and HAMER, in PNAS 1981, 78, p7398–7402, whereby a vector of lower molecular weight can be obtained.

It is possible, on the other hand, after having inserted the poliovirus VP1 sequence within the VP1 gene of the SV40 (for example at the EcoRI site), to remove the reminder of the SV40 nucleotide sequences which separate VP1 of the poliovirus from AUG of the VP1 of SV40 (for example upon using the enzyme Bal 31, after opening at the AccI site). It is noted that the sequence of the nucleotides at the level of the VP1 AUG of the SV40 is: ATG.GCC . . . (codons of the two first VP1 amino acids).

Now, the sequence of the polioviral cDNA after cleavage at the level of the HaeIII site (as described in IIa) is: TA.GCA.CAG.GCC . . . (codons of the three last amino acids of VP3 and of the first amino acid of VP1 of the poliovirus).

The addition of an EcoRI linker (BIOLABS) in front of this sequence by the ligase DNA results in the formation of a new sequence:

CGG .AAT.TCC.GTA.GCA.CAG.GGG . . . (VP1 sequence).

The ligation is followed by digestion with the EcoRI enzyme, then by filling of the 3' end by DNA polymerase I of *E. coli* in the presence of the four deoxyribonucleoside-tri-phosphates. This leads to the production of an entirely bicatenarised end whose sequence is: AAT.TCC.GTA.GCA.CAG.GGG . . . (VP1 sequence of the poliovirus). The ligation of this DNA in a SV40 vector, behind the codon of the second amino acid of VP1 of the SV40,enables a sequence in phase to be recreated:

A<u>TG.GCC.A</u>AT.TCC.GTA.GCA.CAG.GGG.
    └─SV40─┘  └─linker─┘ └─poliovirus─┘ in which the underlined nucleotides (TGGCCA) form a BalI site which existed neither in the SV40 vector nor in the VP1 fragment of poliovirus inserted, and which hence enables the univocal selection of a "SV40-poliovirus" recombinant in which the sequence of the poliovirus VP1, preceded by that of five amino acids, is inserted, in phase, behind that of the two first VP1 amino acids of the SV40.

(d) Animal virus promoters borne by bacterial plasmids

This is the case of plasmids bearing promoters of the gene of thymidine-kinase of the virus of herpes (pAGO), of the gene of the HBS antigen of B hepatitis virus (pAC-2 or pAC-14) or of the early or late genes of the adenovirus 2, etc. The insertion of the VP1 fragment of the poliovirus behind the AUG of the cloned viral gene with its promoter provides for the expression thereof into the animal cell (after transfection, microinjection or cell-protoplast fusion), or for the transcription in vitro by an extract of animal cells, (HeLa cell or VERO cells) with the consequent synthesis of the corresponding RNA messenger.

It may be mentioned that an advantageous way to obtain the initial SV 40 vector is to make use of the cloned recombinant obtained beforehand by insertion of SV 40 in the BamHI site of a plasmid such as pML2 or pBR327 after deletion in said plasmids of their EcoRI site and of that of their AccI site located initially at the 651 position of said plasmids.

IV—DETECTION OF THE EXPRESSION OF VP 1

The expression of the recombinant plasmids bearing the fragment VP 1 and capable of expressing it, i.e. to induce the synthesis of VP 1, is detected by various methods of immunological analysis bringing into play the use of antipoliovirus immunoserum:

mono or polyclonal neutralizing serums, prepared by injection into the animal of virus fixed with formol (serums of D specifity);

non neutralizing serums prepared by injection into the animal of the virus dissociated by heat in the absence of formol, or of empty viral capsids (serums of C specifity);

capsidal anti-protein serums (VP0, VP1, VP2 or VP3) of the poliovirus, obtained by injection into the animal of capsidal proteins prepared by electroelution after separation on polyacrylamide-SDS gel from virions dissociated with SDS and with heat.

The serums are used in immuno-precipitation tests on bacterial extracts premarked with methionine $^{35}S$, or in radio-immunological tests on replicas with IgG marked with $125_I$. These tests are also usable with extracts of animal cells.

V—PROPERTIES OF VP 1

The VP1 protein produced by the above methods is purified by a conventional technology such as, for example, affinity chromatography.

The VP1 protein, synthesized under the various condiitons described can be coupled to a "carrier", that is to say a natural protein or a synthetic polypeptide having a sufficient molecular weight for the conjugate formed to be capable of inducing in vivo antibody production by conventional techniques. It can be reacted with antipoliovirus antibodies. It is immunogenic and when innoculated in the animal, it induces antipoliovirus antibody synthesis.

In addition, it is possible to use it as a reagent for diagnosis and the titration of antipoliomyelitic antibodies. The DNA sequence according to the invention, particularly if labelled, say radioactively, can itself be used as a hybridation probe enabling the detection of the presence of poliovirus RNA or of the corresponding cDNA in a biological specimen.

Thus the invention also concerns a process for the detection of poliovirus RNA or DNA in a biological sample, which process comprises extracting the DNA contents of said sample contacting it with the hybridization probe, under suitable hybridization conditions, recovering the hybrid formed, if any.

Any conventional hybridization technique and isolation technique of the hybrids can be resorted to.

The invention relates naturally to all equivalent DNA sequences resulting in expression products endowed with equivalent immunological properties, such as revealed, for example, by the capacity of antibodies induced by the equivalent expression product to react with the expression product of the DNA fragments more particularly described and vice versa. In particular, the invention extends to DNA sequences which can differ from those which have been more particularly described, by deletions, additions or substitutions of nucleic acids, to the extent where the immunological properties of the resulting expression products are substantially equivalent too.

The invention relates finally to the expression products themselves such as produced by suitable microorganisms transformed by vectors (plasmids or phages) comprising an insert constituted by one of the abovesaid DNA fragments or their equivalents.

We claim:

1. A DNA fragment which codes for a protein that can form a complex with neutralizing antibodies to poliovirus and that has a nucleotide sequence coding for a poliovirus VP-1 protein, wherein said nucleotide sequence is selected from the group consisting of: (a) a first nucleotide sequence extending from the position 2243 to the position 3417 of cDNA corresponding to a PV-1 type poliovirus genome as shown in FIGS. 3 and 4, said first sequence being bounded by two PstI sites; (b) a second nucleotide sequence extending from the position 2472 to the position 3421 of cDNA corresponding to a PV-1 type poliovirus genome as shown in FIGS. 3 and 4, said second sequence being bounded by HaeII and PstI sites; and (c) a third nucleotide sequence extending from the position 2248 to the position 3421 of cDNA corresponding to a PV-1 type poliovirus genome as shown in FIGS. 3 and 4; and (d) a fourth nucleotide sequence extending from the position 2480 to the position 3385 of cDNA corresponding to a PV-1 type poliovirus genome as shown in FIGS. 3 and 4.

2. The DNA of claim 1, wherein the fragment is the nucleotide sequence extending from the position 2248 to the position 3421 of the cDNA corresponding to a PV-1 type poliovirus genome.

3. The DNA fragment of claim 1, wherein the fragment is the nucleotide sequence extending from the 2480 position to the 3385 position of the cDNA corresponding to a PV-1 type poliovirus genome.

4. A modified vector, containing a heterologous insert consisting essentially of a DNA fragment according to claim 21.

5. The modified vector of claim 4 which is a plasmid.

6. A recombinant DNA which comprises a promoter and a nucleotide sequence, under the control of said promoter, and an insert consisting essentially of a DNA fragment according to claim 1 inserted in said nucleotide sequence.

7. The recombinant DNA of claim 6 wherein said promoter and said nucleotide sequence originate from SV40 DNA.

8. The DNA fragment of claim 1 wherein the fragment is the nucleotide sequence extending form the position 2243 to the position 3417 of the cDNA corresponding to a PV-1 type poliovirus, genome said sequence being bounded by two Pst I sites as shown in FIGS. 3 and 4.

9. The DNA fragment of claim 1, wherein the fragment is the nucleotide sequence extending from the position 2472 to the position 3421 of the cDNA corresponding to a PV-1 type poliovirus, genome said sequence being bounded by Hae II and Pst I sites as shown in FIGS. 3 and 4.

* * * * *

UNITED STATES PATENT AND TRADEMARK OFFICE
CERTIFICATE OF CORRECTION

PATENT NO. : 4,968,627
DATED : NOVEMBER 6, 1990
INVENTOR(S) : MARC GIRARD ET AL.

It is certified that error appears in the above-identified patent and that said Letters Patent is hereby corrected as shown below:

In column 8, line 65, claim 1, please delete "that" and insert --which--.

In column 10, line 3, claim 4, please delete "21" and insert --1--.

Signed and Sealed this

Twenty-eighth Day of April, 1992

Attest:

HARRY F. MANBECK, JR.

*Attesting Officer*  *Commissioner of Patents and Trademarks*